(12) United States Patent
Burdick et al.

(10) Patent No.: US 6,214,769 B1
(45) Date of Patent: Apr. 10, 2001

(54) HERBICIDAL N-[(1,3,5-TRIAZIN-2-YL)-AMINOCARBONYL]-BENZENESULFONAMIDES

(75) Inventors: Bruce Burdick, Plattsvurg, MO (US); Terance James, Vegreville (CA); Terry R. Wright, Apple Valley, MN (US); Bruce Kirksey, Lake Village, AR (US)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 09/568,197

(22) Filed: May 9, 2000

(51) Int. Cl.$^7$ .................. A01N 43/64; A01N 47/36
(52) U.S. Cl. .................. 504/134; 504/212; 504/213
(58) Field of Search .................. 504/134, 212, 504/213

(56) References Cited

U.S. PATENT DOCUMENTS

| | | | | |
|---|---|---|---|---|
| 5,478,789 | * | 12/1995 | Mayer et al. | 504/212 |
| 5,488,029 | * | 1/1996 | Hamprecht et al. | 504/212 |
| 6,043,196 | * | 3/2000 | Mayer et al. | 504/212 |

FOREIGN PATENT DOCUMENTS

9965314 * 12/1999 (WO) .

* cited by examiner

Primary Examiner—Jose' G. Dees
Assistant Examiner—Alton Pryor
(74) Attorney, Agent, or Firm—Alston & Bird LLP

(57) ABSTRACT

A method is provided for controlling weeds resistant to acetolactate synthase (ALS)-inhibiting herbicides that includes applying to the locus where control is desired a herbicidally effective amount of a compound of formula I

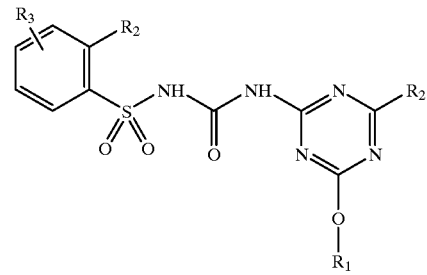

wherein $R_1$ is lower alkyl;

$R_2$ is $CF_3$; and $R_3$ is hydrogen or lower alkyl, or its agriculturally useful salts.

25 Claims, No Drawings

HERBICIDAL N-[(1,3,5-TRIAZIN-2-YL)-AMINOCARBONYL]-BENZENESULFONAMIDES

FIELD OF THE INVENTION

This invention relates to methods for controlling weeds using herbicides, in particular to methods of controlling weeds resistant to acetolactate synthase (ALS)-inhibiting herbicides.

BACKGROUND OF THE INVENTION

Four chemistry classes of acetolactate synthase (ALS)-inhibiting herbicides have been developed and are commercially available for agronomic weed control. They are sulfonylureas such as chlorsulfuron (e.g., GLEAN® from DuPont), imidazolinones such as imazethapyr (e.g., PURSUIT® from American Cyanamid Co.), triazolopyrimidines such as flumetsulam (e.g., BROADSTRIKE® from DowElanco), and pyrimidinylthiobenzoates such as pyrithiobac (e.g., STAPLE® from DuPont). Because of their low use rates, low mammalian toxicity, good crop selectivity, and high efficacy on target weed species, these herbicides have gained widespread use and popularity in weed control in, e.g., corn, soybeans, wheat, barley, cotton, sorghum, rice, and many other crops. Currently, a wide variety of ALS-inhibiting herbicides are commercially available or under development.

However, weed resistance has recently become a great concern in the industry. Weed resistance to ALS-inhibiting herbicides was first recognized five years after the commercial launch of the sulfonylurea herbicide, chlorsulfuron. See Mallory-Smith et al. *Weed Tech*. 4:163–168 (1990). Poor rotation of herbicides to dissimilar modes of action, the high efficacy of ALS-inhibiting herbicides, and the relatively high frequency of naturally occurring mutations have been the contributory factors for the widespread weed resistance to ALS-inhibiting herbicides. Many weeds have developed such resistance. In fact, the number of weed species resistant to ALS-inhibiting chemistries is second only to inhibitors of Photosystem II (e.g., triazines). See Heap, *Pesticide Science* 51:235–234 (1997).

Based on the analysis of the resistant weeds selected from natural weed populations, mutations at five different positions in the primary ALS peptide sequence have been identified to be responsible for ALS-inhibiting herbicide resistance. As summarized in Table 1, each one of the five mutations has a unique cross-class resistance characteristic.

TABLE 1

Cross-Class Resistance to ALS-Inhibiting Herbicides

| Amino acid position of mutation* | ALS-Inhibiting Herbicide Classes | | | |
|---|---|---|---|---|
| | Sulfonylureas | Imidazolinones | Triazolopyrimidines | Pyrimidinylthiobenzoates |
| $A_{122}$ | | R | | |
| $P_{197}$ | R | | R | |
| $A_{205}$ | R | R | R | R |
| $W_{574}$ | R | R | R | R |
| $S_{653}$ | R | | | R |

*refers to the amino acid equivalent position in *Arabidopsis thaliana*

The level of resistance by a weed species having a particular mutation may vary with individual members in one ALS-inhibiting herbicide class. Nevertheless, in general the cross class resistance remains consistent. In other words, if a particular weed is resistant to one member of a particular ALS-inhibiting herbicide class, it will be resistant to all members of that class.

Certain other herbicides which control weeds by a mode of action other than inhibiting acetolactate synthase may be useful in controlling weeds resistant to ALS-inhibiting herbicides. However, none of them possesses all the desirable attributes ALS-inhibiting herbicides have, i.e., low mammalian toxicity, low use rates, good crop selectivity, and high efficacy.

SUMMARY OF THE INVENTION

The present invention provides a method for controlling ALS-inhibiting herbicide resistant weeds using a compound which exhibits the desirable characteristics of low mammalian toxicity, low use rate, good crop selectivity, and high efficacy.

The method of this invention utilizes the herbicidal activity of the N-[(1,3,5-triazin-2-yl)-aminocarbonyl]-benzenesulfonamide compounds of formula I

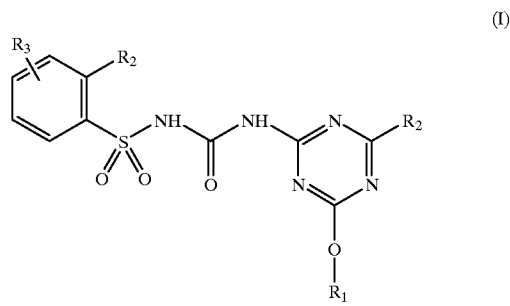

(I)

wherein
  $R_1$ is lower alkyl (e.g., $C_{1-5}$ alkyl such as $CH_3$, $C_2H_5$, and $C_3H_7$);
  $R_2$ is trihalomethyl (e.g., $CF_3$, $CCl_3$, and $CBr_3$);
  $R_3$ is hydrogen or lower alkyl (e.g., $C_{1-5}$ alkyl such as $CH_3$, $C_2H_5$, and $C_3H_7$), or agriculturally useful salts thereof.

The present compounds bear great similarity to sulfonylurea herbicides in chemical structure, and thus would be expected to exhibit weed control properties similar to those of sulfonylurea herbicides. In addition, as discussed above, because of the cross class resistance phenomena, weeds resistant to sulfonylureas would be expected to be resistant to the present compounds as well. Nevertheless, it has been surprisingly discovered that compounds of formula I are highly effective in controlling not only weeds resistant to sulfonylurea herbicides but also weeds resistant to other ALS-inhibiting herbicide classes.

Accordingly, the method of this invention comprises applying a herbicidally effective amount of a compound of formula I, or agriculturally useful salts thereof, to control weeds resistant to an acetolactate synthase (ALS)-inhibiting herbicide.

In a preferred embodiment, a herbicidally effective amount of the compound 1-[(4-methoxy-6-trifluoromethyl)-1,3,5-triazin-2-yl]-3-(2-trifluoromethyl-benzenesulfonyl)-urea or an agriculturally useful salt thereof, is applied to inhibit the undesirable growth of ALS-inhibiting herbicide resistant weeds.

In another embodiment of this invention, a compound of formula I is used in combination with one or more herbicides having a different mode of herbicidal action than inhibiting acetolactate synthase. Non-limiting examples of such one or more herbicides include auxinic herbicides, auxin transport inhibitors, photosynthesis inhibitors, and cell division inhibitors.

The N-[(1,3,5-triazin-2-yl)-aminocarbonyl]-benzenesulfonamide compounds used in the method of this invention are highly effective in controlling weeds resistant to ALS-inhibiting herbicides while exhibiting desirable levels of mammalian toxicity, use rate and crop selectivity that are comparable to those of ALS-inhibiting herbicides. Therefore, the present invention provides an effective method for controlling ALS-inhibiting herbicide resistant weeds and, when properly utilized in combination with other herbicides, for preventing the development of new ALS-inhibiting herbicides resistant weeds.

In addition, often in a particular locus, ALS inhibitor resistant weeds develop from, and cohabit with, ALS inhibitor sensitive wild type weeds. The compounds used in this invention are effective against ALS inhibitor sensitive weeds as well as ALS inhibitor resistant weeds. Thus, the method of this invention is significantly more effective in controlling an entire weed population in a particular locus than methods in the art using conventional ALS-inhibiting herbicides.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

The present invention provides a method for controlling weeds which comprises applying to the locus where control is desired a herbicidally effectively amount of a compound of formula I

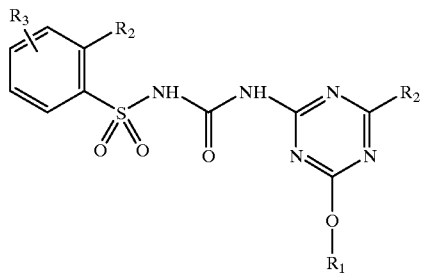

(I)

wherein $R_1$ is lower alkyl (e.g., $CH_3$, $C_2H_5$, and $C_3H_7$);

$R_2$ is trihalomethyl (e.g., $CF_3$, $CCl_3$, and $CBr_3$);

$R_3$ is hydrogen or lower alkyl (e.g., $CH_3$, $C_2H_5$, and $C_3H_7$), or an agriculturally useful salt thereof. As a result of using these compounds, the weeds at the locus are controlled.

Examples of compounds of Formula I include:

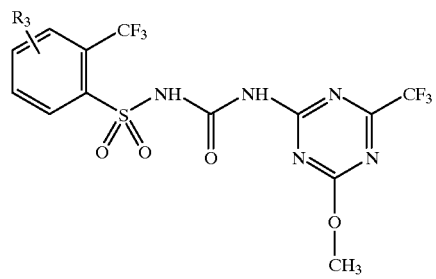

or the sodium salts thereof, where $R_3$ is hydrogen, 3-methyl, 4-methyl, 5-methyl, 6-methyl, 3-ethyl, 4-ethyl, 5-ethyl, 6-ethyl, and the like.

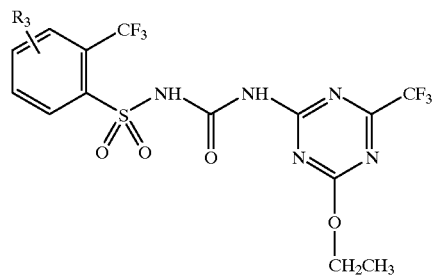

or the sodium salts thereof, where $R_3$ is hydrogen, 3-methyl, 4-methyl, 5-methyl, 6-methyl, 3-ethyl, 4-ethyl, 5-ethyl, 6-ethyl, and the like.

Advantageously, a compound in Table 2 below is used in the method.

TABLE 2

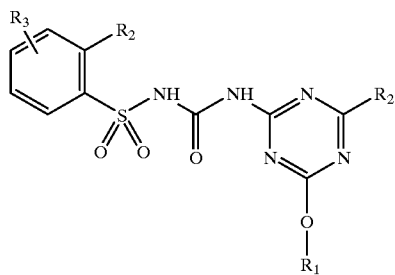

| Active ingredient no. | $R^1$ | $R^2$ | $R^3$ | mp [° C.] |
|---|---|---|---|---|
| 1 | $CH_3$ | $CF_3$ | H | 164–169 |
| 2 | $CH_3$ | $CF_3$ | H | 165 (decomp.) Na salt |
| 3 | $CH_3$ | $CF_3$ | 6-$CH_3$ | 149–150 |
| 4 | $CH_3$ | $CF_3$ | H | 211 (decomp.) Na salt |

The method of this invention is particularly useful in controlling ALS-inhibiting herbicide resistant weeds. However, it is to be understood that ALS-inhibiting herbicide sensitive weeds can also be effectively controlled by the method. As such, the method of this invention can be applied to any locus to prevent the growth of, and/or to damage vegetation of the entire weed population at the locus. The weed population at a particular locus to be treated may include ALS inhibitor resistant weeds, sensitive weeds, or both. In any event, as will be apparent from the description and the examples below, the method of this invention is significantly more effective than prior art methods using conventional ALS inhibitors.

Acetolactate synthase (ALS)-inhibiting herbicides are generally known and many are commercially available for agronomic weed control. As described above, four chemistry classes of ALS-inhibiting herbicides have been developed and applied in weed control, including sulfonylureas, imidazolinones, triazolopyrimidines, and pyrimidinylthiobenzoates. Non-limiting examples of sulfonylurea herbicides include amidosulfuron, azimsulfuron, bensulfuron, chlorimuron, chlorsulfuron, cinosulfuron, cyclosulfamuron, ethametsulfuron, ethoxysulfuron, fenpyrsulfuron, flazasulfuron, flupyrsulfuron, halosufuron, and imazosulfuron. Examples of imidazolinones include imazapic, imazamethabenz, imazamethapyr, imazamox, imazapyr, and imazethapyr. Exemplary pyrimidinylthiobenzoates include bispyribac, pyribenzoxim, and pyriminobac. Commercially available triazolopyrimidine herbicides include, e.g., cloransulam, diclosulam, florasulam, flumetsulam, and metosulam.

Weeds resistant to one or more of these ALS-inhibiting herbicides have been found in, e.g., Blackgrass (*Alopecurus myosuroides*), Rigid Ryegrass (*Lolium rigidum*), Prickly Lettuce (*Lactuca serriola*), Kochia (*Kochia scoparia*), Russian Thistle (*Salsola iberica*), Perennial Ryegrass (*Lolium perenne*), Common cocklebur (*Xanthium strumarium*), Palmer Amaranth (*Amaranthus palmeri*), Smooth Pigweed (*Amaranthus hybridus*), Smallflower Umbrella Sedge (*Cyperus difformis*), California Arrowhead (*Sagittaria montevidensis*), Common Waterhemp (*Amaranthus rudis*), Shattercane (*Sorghum bicolor*), Redroot Pigweed (*Amaranthus retroflexus*), Prickly Sida (*Sida spinosa*), Italian Ryegrass (*Lolium multiflorum*), Giant Foxtail (*Setaria faberi*), Robust White Foxtail (*Setaria viridis var. robusta-alba Schreiber*), Common Sunflower (*Helianthus annuus*), Redstem (*Ammannia auriculata*), Yellow Foxtail (*Setaria lutescens*), Ricefield Bulrush (*Scirpus mucronatus*), and Giant Ragweed (*Ambrosia trifida*)

As used herein, the meaning of the term "weed resistant to an acetolactate synthase (ALS)-inhibiting herbicide" is not limited to the resistant biotypes of the above species. Rather, it is inclusive and is intended to mean any weed biotype that is resistant to at least one of ALS-inhibiting herbicides, while certain other biotypes of the same species are sensitive to the ALS-inhibiting herbicide. It is also intended to mean any weed biotype that is resistant to herbicides in one ALS-inhibiting herbicide class, but sensitive to at least one herbicide of another ALS-inhibiting herbicide class. In addition, "resistant to an ALS-inhibiting herbicide" means that a particular weed biotype cannot be "controlled" by the ALS-inhibiting herbicide.

As used herein, the term "controlled" or "controlling" is intended to mean that when a herbicide is applied to a locus of a weed, the percent control of the weed at the locus as determined based on the phytotoxicity data collected at the locus, is at least about 70%, normally at least about 75%. Preferably, the percent control is at least about 80%, more preferably at least about 85%, even more preferably at least about 90%, and most preferably at least about 95%. The method used to measure control is similar to the 0 to 100 rating system (100 means no emergence of the plants or complete destruction of at least the above-ground parts and 0 means no damage or normal course of growth.) described in *Research Methods in Weed Science*, Truelove, Ed., $2^{nd}$ edition, Southern Weed Science Society, Auburn University, Auburn, Ala., 1977.

As described above, a number of amino acid equivalents (or mutations) in plant acetolactate synthase that confer resistance to ALS inhibitors in naturally selected plants have been identified. As used herein, "amino acid equivalent" refers to an amino acid in the protein sequence of the acetolactate synthase of a particular resistant weed biotype that is different from the corresponding amino acid in sensitive weed biotypes. The amino acid position is named in accordance with the amino acid equivalent position in *Arabidopsis thaliana*. For example, it has been found that when the amino acid alanine at the position 122 ($A_{122}$) of the ALS protein of sensitive plants is changed to threonine ($A_{122}T$), the plant typically becomes resistant to the herbicides in the imidazolinone chemistry class. It has also been discovered that sensitive weeds have a proline at the position 197 ($P_{197}$). In contrast, when a weed has an amino acid equivalent of serine ($P_{197}S$), threonine ($P_{197}T$), arginine ($P_{197}R$), leucine ($P_{197}L$), alanine ($P_{197}A$), histitine ($P_{197}H$), or glutamine ($P_{197}Q$), the weed is typically resistant to sulfonylureas and triazolopyrimidines. Weeds having an alanine to valine mutation ($A_{205}V$), or tryptophan to leucine ($W_{574}L$), cystine ($W_{574}C$) or serine ($W_{574}S$) mutation, typically are resistant to all four chemistry classes of ALS-inhibiting herbicides. In addition, weeds with an serine to asparagine ($S_{653}N$) mutation typically are resistant to imidazolinones and pyrimidinylthiobenzoates. See Mazur and Falco, *Ann. Rev. Plant Physiol. Mol. Biol.* 40:441–470 (1989); Ott et al. *J. Mol. Biol.* 263:359–368 (1997). The method of this invention can be used in controlling weeds having any one of such amino acid equivalents, and generally can be used to control weeds having two or more of the above-described amino acid equivalents.

In a preferred embodiment, a herbicidal composition comprising a herbicidally effective amount of a compound of formula I, wherein $R_1$ is methyl, $R_2$ is trifluoromethyl, and $R_3$ is hydrogen, i.e., the compound 1-[(4-methoxy-6-trifluoromethyl)-1,3,5-triazin-2-yl]-3-(2-trifluoromethyl-benzenesulfonyl)-urea, is applied to the locus where control is desired.

In another embodiment of the invention, in addition to a herbicidally effective amount of an N-[(1,3,5-triazin-2-yl)-aminocarbonyl]-benzenesulfonamide of formula I set forth above, preferably 1-[(4-methoxy-6-trifluoromethyl)-1,3,5-triazin-2-yl]-3-(2-trifluoromethyl-benzenesulfonyl)-urea, a herbicidally effective amount of one or more additional herbicidal compounds having a different mode of herbicidal action than ALS inhibitors are also applied to the same locus, either separately or in a mixture with the N-[(1,3,5-Triazin-2-yl)-aminocarbonyl]-benzenesulfonamide compound of formula I. Preferably such herbicidal compounds are synthetic auxins, auxin transport inhibitors, inhibitors of photosynthesis at photosystem II, and inhibitors of cell division in weeds. Examples of synthetic auxins include benzoic acids such as dicamba, chloramben and TBA; pyridine carboxylic acids such as clopyralid, fluroxypyr, picloram, and triclopyr; benazolin-ethyl; phenoxy-carboxylic acids such as clomeprop, dichlorprop, and mecoprop; and quinoline carboxylic acids, such as quinclorac and quinmerac. Exemplary auxin transport inhibitors are naptalam and diflufenzopyr-sodium. Cell division inhibitors include, but are not limited to, chloroacetamides (e.g., acetochlor, alachlor, butachlor, dimethachlor, dimethanamid, metazachlor, metolachlor, pretilachlor, propachlor, propisochlor, thenylchlor), acetamides (e.g., diphenamid, napropamide, naproanilide), oxyacetamides (e.g., flufenacet, mefenacet and fluthiamid), tetrazolinones (e.g., fentrazamide), anilofos, cafenstrole, and piperophos, and pronamide. Photosynthesis inhibitors include bentazon, bromofenoxim, bromoxynil, ioxynil, and pyridafol.

Advantageously, the additional herbicidal compounds are capable of controlling weeds through a different mode of action while having an overlapping weed control spectra with the N-[(1,3,5-triazin-2-yl)-aminocarbonyl]-benzenesulfonamide compounds of formula I. The combination of the high efficacy and low use rate of the N-[(1,3,5-triazin-2-yl)-aminocarbonyl]-benzenesulfonamide compounds of formula I and the relatively low probability of significant resistance to the additional herbicides provides an excellent weed resistance management tool for preventing the development or selection of new herbicide resistant weed populations while also providing superior weed control.

In addition, it may also be advantageous to apply the compounds of formula I, alone or in combination with other herbicides, as a mixture with other crop protection agents, for example with pesticides, fungicides, or bactericides. Optionally, mineral salt solutions which are useful as nutrient and trace element supplements, and nonphytotoxic oils and oil concentrates may also be combined in the mixture.

The compounds of formula I can be applied either preemergence or postemergence to the weed loci. If the active ingredients are not well tolerated by certain crops, it is possible to use application methods in which the herbicides are sprayed with the aid of sprayers in such a way that the leaves of the sensitive crops are as far as possible not affected while the active ingredients reach the leaves of undesirable plants. Safeners known in the art may also be used. The application rates of the active ingredients are from 0.001 to 1.0, preferably from 0.01 to 0.5, kg/ha, depending on the aim of control, the season, the target plants and the stage of growth.

The method of this invention can be used in controlling ALS inhibitor resistant weeds in a number of crops. The method is especially suited for cereal crops such as corn, soybean, wheat, barley, cotton, sorghum, and rice. Examples of suitable crops include the following:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *Rapa* | fodder beets |
| *Brassica napus* var. *napus* | rapeseed |
| *Brassica napus* var. *napobrassica* | swedes |
| *Brassica apa* var. *silvestris* | beets |
| *Camellia sinensis* | tea plants |
| *Carthamus tinctorius* | safflower |
| *Citrus limon* | lemons |

-continued

| Botanical name | Common name |
| --- | --- |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermudagrass in turf and lawns |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* Spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifrra* | grapes |
| *Zea mays* | Indian corn, sweet corn, maize |

The novel sulfonylureas of formula I can be obtained by various methods which are described in the literature. Particularly advantageous methods (A–D) are described in detail below by way of example.

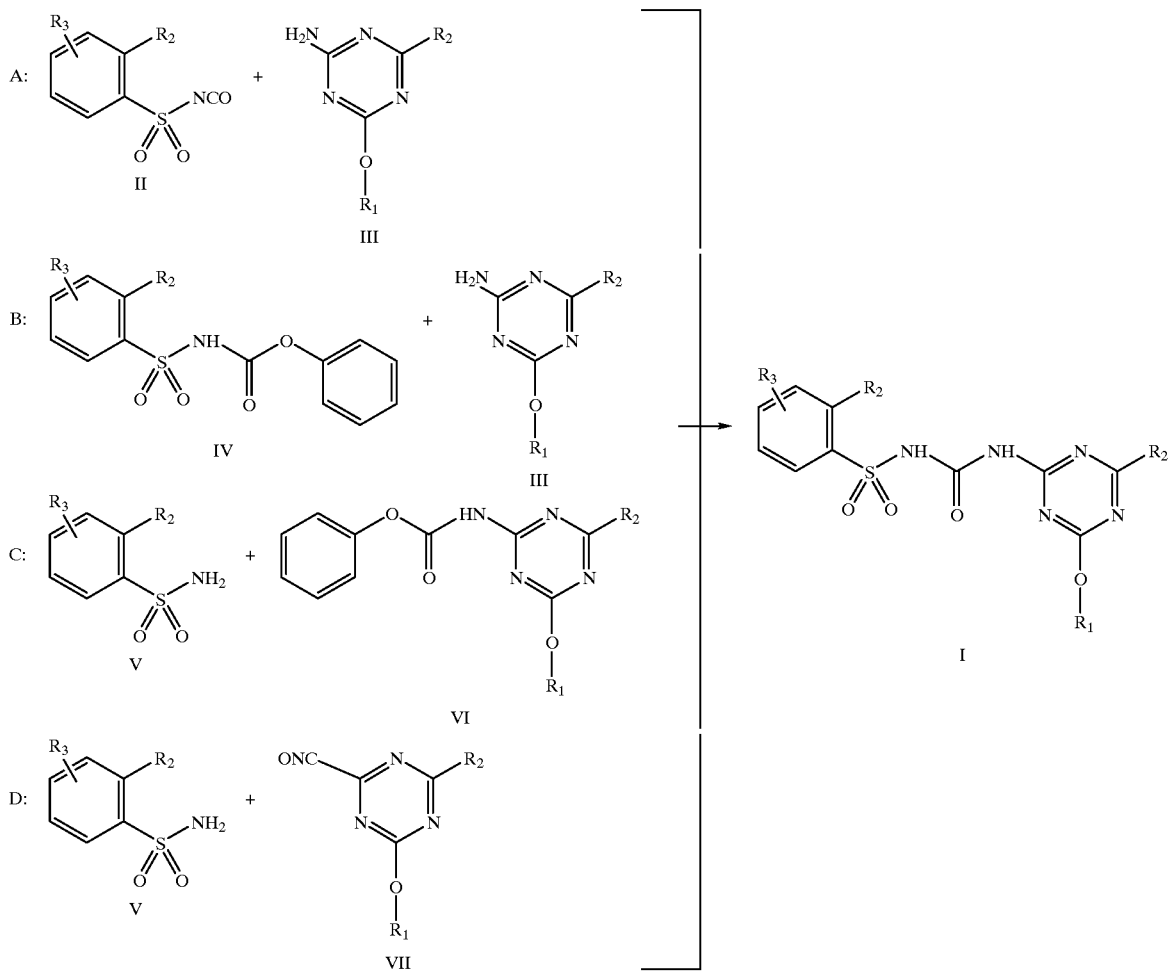

METHOD A: A sulfonyl isocyanate II is reacted in a conventional manner (EP-A-162 723) with about the stoichiometric amount of a 2-amino-1,3,5-triazine derivative III at from 0° C. to 120° C., preferably from 10° C. to 100° C. The reaction can be a continuous or batch process under atmospheric or superatmospheric pressure (up to 50 bar), preferably from 1 to 5 bar.

Solvents and diluents which are inert under the particular reaction conditions are advantageously used for the reactions. Examples of suitable solvents are halohydrocarbons, in particular chlorohydrocarbons, e.g. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene, and 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane, thioanisole and .beta.,.beta.'-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, e.g. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, e.g. ethyl acetate, ethyl acetoacetate and isobutyl acetate; amides, e.g. forms/aide, methylformamide and dimethylformamide; ketones, e.g. acetone and methyl ethyl ketone, and corresponding mixtures. The solvent is advantageously used in an amount of from 100 to 2000%, preferably from 200 to 700% by weight, based on the starting material II.

The compound II required for the reaction is generally used in about an equimolar amount (for example in an amount of from 80 to 120%, based on the particular starting material III, of the stoichiometric amount). The starting material III may be initially taken in one of the abovementioned diluents and the starting material II added.

Advantageously, however, the process for the preparation of the compounds of the formula I is carried out by a method in which the starting material II, if necessary in one of the above mentioned diluents, is initially taken and the starting material III is then added.

To complete the reaction, stirring is carried out for a further 20 minutes to 24 hours at from 0° to 120° C., preferably from 10° to 100° C., after the addition of the components.

A tertiary amine, e.g. pyridine, $\alpha,\beta,\gamma$-picoline, 2,4- and 2,6-lutidine, 2,4,6-collidine, p-dimethylaminopyridine, trimethylamine, triethylamine, tri-n-propylamine, 1,4-diazabicyclo[2.2.2]octane [DABCO] or 1,8-diazabicyclo [5.4.0]undec-7-ene, can advantageously be used as a reaction accelerator in an amount of from 0.01 to 1 mol per mole of starting material II.

The end product I is isolated from the reaction mixture in a conventional manner, for example after distilling off the solvent or directly by filtration under suction. The remaining residue may furthermore be washed with water or dilute acid to remove basic impurities. However, the residue can also be dissolved in a water-immiscible solvent and washed in the manner described. The desired end products are obtained here in pure form; if necessary, they can be purified by recrystallization, stirring in an organic solvent which takes up the impurities or chromatography.

This reaction is preferably carried out in acetonitrile, methyl tert-butyl ether, toluene or methylene chloride in the presence of from 0 to 100, preferably from 0 to 50, mol equivalents of a tertiary amine, such as 1,4-diazabicyclo[2, 2,2]octane or triethylamine.

METHOD B: A corresponding sulfonylcarbamate of the formula IV is reacted in a conventional manner (EP-A-120 814, EP-A-101 407) with a 2-amino-1,3,5-triazine derivative III in an inert organic solvent at from 0° to 120° C., preferably from 10° to 100° C. Bases, such as tertiary amines, may be added here, with the result that the reaction is accelerated and the product quality improved.

Suitable bases for this purpose are, for example, tertiary amines as stated under A, in particular triethylamine or 1,4-diazabicyclo[2.2.2]octane, in an amount of from 0.01 to 1 mol per mole of starting material IV.

Advantageously used solvents are those stated under A.

The solvent is used in an amount of from 100 to 2,000, preferably from 200 to 700, % by weight, based on the starting material IV.

The compound IV required for the reaction is generally used in about an equimolar amount (for example in an amount of from 80 to 120%, based on the particular starting material III, of the stoichiometric amount). The starting material IV may be initially taken in one of the above mentioned diluents and the starting material III then added.

However, it is also possible initially to take the starting material III in one of the stated solvents or diluents and to add the sulfonylcarbamate IV.

In both cases, a base may be added as a catalyst before or during the reaction.

The end product I can be obtained from the reaction mixture in a conventional manner, as stated under A.

METHOD C: A sulfonamide of the formula V is reacted in a conventional manner (EP-A-141 777 and EP-A-101 670) with about the stoichiometric amount of a phenyl carbamate VI in an inert organic solvent at from 0° to 120° C., preferably from 20° to 100° C. The reaction is carried out continuously or batchwise at atmospheric or superatmospheric pressure (up to 50 bar), preferably at from 1 to 5 bar.

Bases such as tertiary amines, which accelerate the reaction and improve the product quality, may be added here. Suitable bases for this purpose are those stated under A, in particular triethylamine, 2,4,6-collidine, 1,4-diazabicyclo [2.2.2]octane [DABCO] or 1,8-diazabicyclo[5.4.0]undec-7-ene (DBU), in an amount of from 0.01 to 1 mol per mole of starting material V.

Advantageously used solvents or diluents are those stated under A.

The solvent is used in an amount of from 100 to 2,000, preferably from 200 to 700, % by weight, based on the educt V.

The compound V required for the reaction is generally used in about an equimolar amount (for example in an amount of 80 to 120%, based on the particular starting materials VI, of the stoichiometric amount). The starting material VI may be initially taken in one of the above mentioned diluents and the starting material V then added.

However, it is also possible initially to take the starting material V in one of the stated solvents and then to add the carbamate VI. In both cases, one of the stated bases may be added as a catalyst before or during the reaction.

To complete the reaction, stirring is carried out for a further 20 minutes to 24 hours at from 0° to 120° C., preferably from 10° to 100° C., in particular from 20° to 80° C., after the addition of the components.

The sulfonylureas of the formula I are isolated from the reaction mixture by the conventional methods, as described under A.

METHOD D: A sulfonamide of the formula V is reacted in a conventional manner (EP-A-234 352) with about the stoichiometric amount of an isocyanate VII in an inert organic solvent at from 0° to 150° C., preferably from 10° to 100° C. The reaction can be carried out continuously or batchwise at atmospheric or superatmospheric pressure (up to 50 bar), preferably at from 1 to 5 bar.

Bases such as tertiary amines, which accelerate the reaction and improve the product quality, may be added before or during the reaction. Suitable bases for this purpose are those stated under A, in particular triethylamine or 2,4,6-collidine, in an amount of from 0.01 to 1 mol per mole of starting material V.

Advantageously used solvents are those stated under A. The solvent is used in an amount of from 100 to 2,000%, preferably from 200 to 700% by weight, based on the educt V.

The compound V required for the reaction is generally used in about the equimolar amount (for example in an amount of from 80 to 120%, based on the educts VII, of the stoichiometric amount). The starting material VII can be initially taken in one of the stated diluents and the starting material V then added. However, it is also possible initially to take the sulfonamide and then to add the isocyanate VII.

To complete the reaction, stirring is carried out for a further 20 minutes to 24 hours at from 0° to 120° C., preferably from 10° to 100° C., in particular from 20° to 80° C., after the addition of the components. The end product I can be obtained from the reaction mixture in a conventional manner, as described under A.

The sulfonyl isocyanates of the formula II which are required as starting materials can be obtained in a conventional manner from the corresponding sulfonamides by phosgenation, as disclosed in e.g. U.S. Pat. No. 4,379,769, which is incorporated herein by reference, or by reaction of the sulfonamides with chlorosulfonyl isocyanate as described in German Laid-Open Application DOS 3,132, 944, which is incorporated herein by reference.

The sulfonylcarbamates of the formula IV were prepared by, or similarly to, conventional reactions, as disclosed in, e.g. EP-A 120 814, which is incorporated herein by reference. However, the sulfonyl isocyanates of the formula II can also be converted into the carbamates of the formula IV in a smooth reaction in an inert solvent, such as ether or dichloromethane.

Carbamates of the formula VI are obtainable by, or similarly to, known reactions (e.g. EP-A 101 670), but they can also be prepared from the corresponding isocyanates VII by reaction with phenol.

The isocyanates of the formula VII are obtained from the amines of the formula III by treatment with oxalyl chloride or phosgene (by a method similar to that described in *Angew. Chem.* 83 (1971), 407 or EP-A 388 873), both of which are incorporated herein by reference.

The sulfonamides can be obtained by reacting the corresponding sulfonyl chlorides with ammonia, as disclosed in, e.g., Houben-Weyl, *Methoden der organischen Chemie*, 9:605 (1955), which is incorporated herein by reference. The sulfonyl chlorides are obtained either by a Meerwein reaction (diazotization of suitable amines and sulfochlorination under catalysis with a copper salt) or by chlorosulfonation of suitable aromatics, for example 2,5-dichlorobenzenesulfonyl chloride from p-dichlorobenzene.

2-Amino-4-methoxy-6-trifluoromethyl-1,3,5-triazine and 2-amino-4-ethoxy-6-trifluoromethyl-1,3,5-triazine are known in the art, e.g., in Yakugaku Zasshi, 95:499 (1975).

The salts of the compounds I are obtainable in a conventional manner. See, e.g., EP-A 304 282 and U.S. Pat. No. 4,599,412. They are obtained by deprotonation of the corresponding sulfonylureas I in water or in an inert organic solvent at from −80° to 120° C., preferably from 0° to 60° C., in the presence of a base. Examples of suitable bases are alkali metal or alkaline earth metal hydroxides, hydrides, oxides or alcoholates, such as sodium, potassium and lithium hydroxide, sodium methylate, ethylate or tert-butylate, sodium and calcium hydride and calcium oxide. Examples of suitable solvents in addition to water are also alcohols such as methanol, ethanol and tert-butanol; ethers such as tetrahydrofuran and dioxane; acetonitrile, dimethylformamide; ketones such as acetone and methyl ethyl ketone; and halogenated hydrocarbons. The deprotonation can be carried out under atmospheric pressure or at up to 50 bar, preferably at from atmospheric pressure to a superatmospheric pressure of 5 bar.

The compounds of the formula I or the herbicides containing them, and their environmentally compatible salts of alkali metals and alkaline earth metals, can control weeds very well in crops such as wheat, rice and corn, without damaging the crops, an effect which occurs particularly at low application rates. They can be used, for example, in the form of directly sprayable solutions, powders, suspensions (including concentrated aqueous, oily or other suspensions or dispersions), emulsions, oil dispersions, pastes, dusting agents, broadcasting agents or granules, by spraying, nebulizing, dusting, broadcasting or pouring. The application forms depend on the intended uses but should in any case ensure the very fine distribution of the novel active ingredients.

The compounds of the formula I are suitable in general for the preparation of directly sprayable solutions, emulsions, pastes or oil dispersions. Suitable inert additives include mineral oil fractions having a medium to high boiling point, such as kerosene or diesel oil, coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone and strongly polar solvents such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates dissolved in an oil or solvent can be homogenized in water by means of wetting agents, adherents, dispersants or emulsifiers. However, concentrates which consist of active ingredient, wetting agents, adherents, dispersants or emulsifiers and possibly solvents or oil and which are suitable for dilution with water can also be prepared.

Suitable surfactants are the alkali metal, alkaline earth metal and ammonium salts of aromatic sulfonic acids (e.g., lignin-, phenol-, naphthalene- and dibutylnaphthalene-sulfonic acids), and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, the condensates of naphthalene or of naphthalenesulfonic acid with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents or dusting agents can be prepared by mixing and milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulose powders and other solid carriers.

The formulations contain in general from 0.1 to 95%, preferably from 0.5 to 90% by weight of active ingredient.

Examples of formulations are:

I. 90 parts by weight of a compound of the formula I are mixed with 10 parts by weight of N-methyl-α-pyrrolidone and a solution which is suitable for use in the form of very small drops is obtained.

II. 20 parts by weight of a compound of the formula I are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of a compound of the formula I are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of a compound of the formula I are dissolved in a mixture which consists of 25 parts by weight of cyclohexanone, 65 parts by weight of a mineral oil fraction boiling within a range of from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of a compound of the formula I are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of a silica gel powder, and the mixture is milled in a hammer mill. By finely distributing the mixture in 20,000 parts by weight of water, a spray liquor which contains 0.1% by weight of the active ingredient is obtained.

VI. 3 parts by weight of a compound of the formula I are mixed with 97 parts by weight of finely divided kaolin. A dusting agent which contains 3% by weight of the active ingredient is obtained in this manner.

VII. 30 parts by weight of a compound of the formula I are thoroughly mixed with a mixture of 92 parts by weight of silica gel powder and 8 parts by weight of paraffin, which was sprayed onto the surface of this silica gel. A formulation of the active ingredient having good adhesion is obtained in this manner.

VIII. 20 parts by weight of a compound of the formula I are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

Herbicidal Activities

The herbicidal action of the N-[(1,3,5-triazin-2-yl)-aminocarbonyl]-benzenesulfonamide of the formula I on the growth of the test plants is demonstrated by the following field trials and greenhouse experiments.

Greenhouse Experiments:

The culture vessels used were plastic flower pots having a capacity of 300 cm$^3$ and containing loamy sand with about 3.0% of humus as the substrate. The seeds of the test plants were sown shallowly and separately according to species and seed source.

For the purposes of the postemergence treatment, directly sown plants grown in the same vessels were selected. Treatments were replicated three times.

The test plants were then treated at a height of growth of approximately 4 cm, with the active ingredients suspended or emulsified in water as a distributing agent. The active ingredients were sprayed through finely distributing nozzles.

The test vessels were placed in a greenhouse, warmer areas (from 20° to 35° C.) being preferred for warmth-loving species and from 10° to 20° C. for those from temperate climates. The test period extended over from 2 to 4 weeks. During this time, the plants were tended and their reactions to the individual treatments were evaluated.

Evaluation was based on a scale from 0 to 100. 100 means complete destruction of at least the above-ground parts and 0 means no damage or normal course of growth. The method is similar to the 0 to 100 rating system disclosed in "Research Methods in Weed Science," 2$^{nd}$ ed., B. Truelove, Ed.; Southern Weed Science Society, Auburn University, Auburn, Ala., 1977.

Field Trials:

Cleaver (*Galium aparine*) trials in spring wheat. Trials were established in spring wheat fields where cleavers resistance to ALS inhibitor herbicides was expected. Plot size was 2 meters×10 meters with four replicates. Treatments were applied in 100 liters/ha of water with a hand-held $CO_2$ pressured sprayer. Treatments were in a randomized complete block design. Crop height was approximately 15–25 cm and cleavers height was 10 to 20 cm at the time of application. Cleaver control was evaluated at 7, 27 and 57 days after treatment using a rating scale in which 0 means no control and 100 equals complete control.

Tall waterhemp (*Amaranthus tuberculatis*) trials in corn. Trials were established in corn fields where waterhemp resistance to ALS inhibitor herbicides was suspected. Plot size was 6.7 ft×30 ft with three replicates. Treatments were applied in 20 gallon/acre of water with a hand-held $CO_2$ pressured sprayer. Trial was a randomized complete block design. Crop height was approximately 12–55 cm and waterhemp height was 1 to 3 cm at the time of application. Waterhemp control was evaluated at from 1 to 5 weeks using a rating scale in which 0 means no control and 100 equals complete control.

Results

In the following tables, the unit term "lb ai/ha" means pounds of active ingredient per hectare, and "g ai/ha" means grams of active ingredient per hectare. "DAT" means days after treatment. The Bayer Codes of the tested plants, and their corresponding common names and botanical names are listed in the following:

| Bayer Code | WSSA Common Name | Genus Species |
| --- | --- | --- |
| AMATU | Tall Waterhemp | *Amaranthus tuberculatis* |
| AMATA | Common Waterhemp | *Amaranthus rudis* |
| GALAP | Catchweed bedstraw | *Galium aparine* |
| KCHSC | Kochia | *Kochia scoparia* |
| AMAPA | Palmer Amaranth | *Amaranthus palmeri* |

The following herbicidal compounds were tested and compared in the trials summarized in Tables 3–7:

| Herbicide | Common Name/Chemical Name | Chemical Family |
| --- | --- | --- |
| Compound A | 1-[(4-methoxy-6-trifluoromethyl)-1,3,5-triazin-2-yl]-3-(2-trifluoromethyl-benzenesulfonyl)-urea | Sulfonylurea |
| Beacon ® | Primisulfuron-methyl (Ciba) | Sulfonylurea |
| Clarity ® | Dicamba (BASF Corp.) | Benzoic Acid |
| Classic ® | Chlorimuron-ethyl (DuPont Agr. Prod.) | Sulfonylurea |
| Exceed ® | Prosulfuron (28.5%) | Sulfonylurea |
|  | Primisulfuron-methyl (28.5%) | Sulfonylurea |
| Glean ® | Chlorsulfuron (DuPont Agr. Prod.) | Sulfonylurea |
| Hornet | Flumetsulam (23.1%) | Triazolopyrimidines |
|  | Clopyralid (62.5%) | Pyridine carboxylic acid |
| Peak ® | Prosulfuron (Ciba) | Sulfonylurea |

-continued

| Herbicide | Common Name/Chemical Name | Chemical Family |
|---|---|---|
| Permit ® | Halosulfuron-methyl (Monsanto Co.) | Sulfonylurea |
| Pursuit ® | Imazethapyr (American Cyanamid Co.) | Imidazolinone |
| Refine Extra ® | Thifensulfuron-methyl + Tribenuron-methyl (DuPont Agr. Prod.) | Sulfonylurea |

1. Control of Waterhemp

As shown in Tables 3 and 4, Compound A gave excellent control (more than 93%) of waterhemp at all rates studied at 7 days after treatment, while Peak®, Permit® and Exceed®, all of which are sulfonylurea herbicides, gave poor control (less than 67%) even at 36 days after treatment. Hornet (a combination of triazolopyrimidine and pyridine carboxylic acid) also did not give good control (31.7% and less). Damage to field corn was minimal and temporary.

TABLE 3

Control Of Waterhemp (*Amaranthus rudis*) In Field Corn

| TREATMENT | RATE (lb ai/a) | PERCENT CONTROL | |
|---|---|---|---|
| | | 16 DAT | 36 DAT |
| Untreated | | 0 | 0 |
| Compound A | 0.027 | 97.0 | 93.3 |
| | 0.036 | 95.7 | 96.7 |
| | 0.045 | 97.7 | 96.0 |
| | 0.054 | 97.0 | 93.3 |
| Peak ® | 0.018 | 50.0 | 31.7 |
| | 0.020 | 53.3 | 35.0 |
| Permit ® | 0.016 | 36.7 | 20.0 |
| | 0.232 | 66.7 | 43.3 |
| Compound A + Clarity | 0.045 0.025 | 96.3 | 93.3 |

TABLE 4

Control Of Waterhemp (*Amaranthus rudis*) In Field Corn

| TREATMENT | RATE (lb ai/a) | PERCENT CONTROL | |
|---|---|---|---|
| | | 7 DAT | 27 DAT |
| Untreated | | 0 | 0 |
| Compound A | 0.054 | 96.7 | 95.7 |
| Permit ® | 0.031 | 36.7 | 31.7 |
| Exceed ® | 0.036 | 50.0 | 46.7 |
| Hornet ® | 0.134 | 31.7 | 26.7 |
| Clarity ® | 0.25 | 96.3 | 91.7 |
| | 0.5 | 99.0 | 97.3 |

2. Control of Cleavers (*Galium aparine*)

Table 5 summarizes the comparison of the herbicidal activities of compound A, sulfonylurea herbicides Glean® and Refine Extra®, and Imidazolinone herbicide Pursuit® on cleavers (*Galium aparine*). While compound A according to this invention and the imidazolinone herbicide Pursuit® gave good control of the *Galium aparine* biotypes tested, the sulfonylurea herbicides Glean®, and Refine Extra® were ineffective in controlling the *Galium aparine* biotypes.

TABLE 5

Control Of Cleavers (*Galium aparine*) in Spring Wheat Field Trials

| | | *Galium aparine* | |
|---|---|---|---|
| TREATMENT | RATE (kg ai/ha) | 27 DAT | 51 DAT |
| Untreated | | | |
| Compound A | 0.05 | 88.8 | 93.5 |
| Compound A | 0.01 | 88.8 | 87.5 |
| Glean ® | 0.015 | 27.5 | 52.5 |
| Refine Extra ® | 0.015 | 0.0 | 0.0 |
| Pursuit ® | 0.05 | 90.0 | 95.0 |

3. Control of Kochia (*Kochia scoparia*)

Compound A of this invention was tested in greenhouse on different biotypes of Kochia, along with several other sulfonylurea herbicides including Glean®, Refine Extra® and Beacon®. As demonstrated in Table 6, while all were effective in controlling *Kochia scoparia*, only the Compound A of this invention can effectively control the Kochia biotypes APC003A, and APC004A. The herbicides Glean®, Refine Extra® and Beacon® were not capable of controlling these biotypes at a commercially acceptable level.

TABLE 6

Control Of Kochia (*Kochia scoparia*) in Greenhouse

| | | KCHSC | | | APC003A | | | APC004A | | |
|---|---|---|---|---|---|---|---|---|---|---|
| TREATMENT | RATE (Kg/ha ai) | 6 DAT | 15 DAT | 20 DAT | 6 DAT | 15 DAT | 20 DAT | 6 DAT | 15 DAT | 20 DAT |
| Untreated | | 0 | 0 | 0 | 0 | 0 | 0 | 0 | 0 | |
| Compound A | 0.05 | 73.3 | 96.0 | 99.0 | 70.0 | 93.3 | 96.0 | 90.0 | 90.0 | 95.0 |
| Glean ® | 0.035 | 63.3 | 96.3 | 100 | 60.0 | 81.3 | 71.7 | 6.7 | 10.0 | 3.3 |
| Beacon ® | 0.020 | 60.0 | 90.0 | 96.7 | 20.0 | 10.0 | 10.0 | 20.0 | 33.3 | 23.3 |

4. Control of *Amaranthus Palmeri* and *Amaranthus Rudis* In Greenhouse

Compound A was compared with the Imidazolinone herbicide Pursuit®, and the sulfonylurea herbicide Classic® for herbicidal activities on Palmer amaranth (*Amaranthus palmeri*) and common waterhemp (*Amaranthus rudis*). As shown in Table 7, while all were effective in controlling the sensitive biotype of Palmer Amaranth, only compound A was capable of controlling the other Palmer Amaranth biotypes (APC072A and APC073A) and the waterhemp biotype (APC071A) at a commercially acceptable level.

TABLE 7

| | | Control Of Palmer Amaranth and in Greenhouse | | | |
| --- | --- | --- | --- | --- | --- |
| TREATMENT | RATE (g/ha ai) | Palmer Amaranth 24 DAT | APC071A Waterhemp 24 DAT | APC072A Palmer Amaranth 24 DAT | APC073A Palmer Amaranth 24 DAT |
| Untreated | | | | | |
| Compound A | 50 | 98 | 93 | 82 | 96 |
| Pursuit ® | 70 | 98 | 27 | 40 | 62 |
| Classic ® | 10 | 94 | 29 | 3 | 47 |

The above experiments clearly demonstrate the effectiveness of the N-[(1,3,5-triazin-2-yl)-aminocarbonyl]-benzenesulfonamide compounds of formula I in controlling broadleaf weeds such as tall waterhemp, common waterhemp, cleavers, Palmer Amaranth, and kochia. In particular, the compounds are highly effective to control weeds resistant to ALS inhibitors. The compounds exhibit high efficacy and low use rates without causing significant damage to the desirable crops including cereal crops.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for controlling a weed resistant to an acetolactate synthase (ALS)-inhibiting herbicide, comprising applying to the locus of said resistant weed a herbicidally effective amount of a compound of the formula I, or agriculturally useful salts thereof,

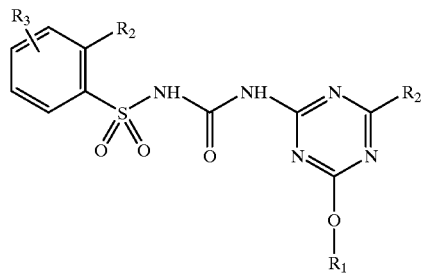

wherein
$R_1$ is lower alkyl;
$R_2$ is trihalomethyl;
$R_3$ is hydrogen or lower alkyl, or an agriculturally useful salt thereof.

2. The method of claim 1, wherein $R_1$ is methyl, $R_2$ is trifluoromethyl, and $R_3$ is hydrogen.

3. The method of claim 1, wherein said weed is resistant to a sulfonylurea herbicide.

4. The method of claim 3, wherein said sulfonylurea herbicide is selected from the group consisting of prosulfuron, halosulfuron, chlorosulfuron, tribenuron, primisulfuron, and chlorimuron.

5. The method of claim 1, wherein said weed is resistant to an imidazolinone herbicide.

6. The method of claim 5, wherein said imidazolinone herbicide is imazethapyr.

7. The method of claim 1, wherein said weed is resistant to a triazolopyrimidine herbicide.

8. The method of claim 7, wherein said triazolopyrimidine herbicide is flumetsulam.

9. The method of claim 1, wherein said weed is selected from the group consisting of *Amaranthus rudis*, *Amaranthus tuberculatis*, *Galium aparine*, *Amaranthus palmeri*, and *Kochia scoparia*.

10. The method of claim 1, further comprising applying to the locus a herbicidally effective amount of one or more herbicidal compounds selected from the group consisting of benzoic acids, phenoxy carboxylic acids, pyridine carboxylic acids, quinoline carboxylic acids, phthalamates, semicarbazones, benzothiadiazinones, nitriles, phenylpyridazines, acetamides, benzamides, chloroacetamides, oxyacetamides, tetrazolinones, anilofos, bromobutide, cafenstrole, piperophos, and diflufenzopyr.

11. The method of claim 1, further comprising applying to the locus a herbicidally effective amount of one or more herbicidal compounds selected from the group consisting of dicamba, diflufenzopyr, bentazon, and dimethenamid.

12. The method of claim 1, wherein the weed is controlled in cereal crops.

13. The method of claim 12, wherein said cereal crop is corn, soybean, wheat, barley, cotton, sorghum, or rice.

14. The method of claim 1, wherein said weed has one or more amino acid equivalents selected from the group consisting of $A_{122}T$, $P_{197}S$, $P_{197}T$, $P_{197}R$, $P_{197}L$, $P_{197}A$, $P_{197}H$, $P_{197}Q$, $A_{205}V$, $W_{574}L$, $W_{574}C$, $W_{574}S$ and $S_{653}N$.

15. The method of claim 1, wherein said weed has an alteration at $P_{197}$ of its acetolactate synthase.

16. A method for controlling a weed resistant to an acetolactate synthase (ALS)-inhibiting herbicide, comprising applying to the locus where control is desired a herbicidally effective amount of 1-[(4-methoxy-6-trifluoromethyl)-1,3,5-triazin-2-yl]-3-(2-trifluoromethyl-benzenesulfonyl)-urea or an agriculturally useful salt thereof to inhibit the undesirable growth of said weed.

17. The method of claim 16, further comprising applying to the locus one or more herbicidal compounds selected from the group consisting of dicamba, diflufenzopyr, bentazon, and dimethenamid.

18. The method claim 16, wherein said weed is resistant to one or more herbicides selected from the group consisting of prosulfuron, halosulfuron, chlorosulfuron, tribenuron, primisulfuron, chlorimuron, imazethapyr, and flumetsulam.

19. The method of claim 16, wherein said weed is resistant to a sulfonylurea herbicide.

20. The method of claim 16, wherein the weed is controlled in cereal crops.

21. The method of claim 16, wherein said weed has one or more amino acid equivalents selected from the group consisting of $A_{122}T$, $P_{197}S$, $P_{197}T$, $P_{197}R$, $P_{197}L$, $P_{197}A$, $P_{197}H$, $P_{197}Q$, $A_{205}V$, $W_{574}L$, $W_{574}C$, $W_{574}S$ and $S_{653}N$.

22. The method of claim 16, wherein said weed has an alteration at $P_{197}$ of its acetolactate synthase.

23. The method of claim 16, wherein said weed is selected from the group consisting of *Amaranthus rudis, Amaranthus tuberculatis, Galium aparine, Amaranthus palmeri*, and *Kochia scoparia*.

24. A method for controlling weeds selected from the group consisting of *Amaranthus palmeri, Amaranthus rudis, Amaranthus tuberculatis*, and *Kochia scoparia*, comprising:

applying to the locus where control is desired a herbicidally effective amount of 1-[(4-methoxy-6-trifluoromethyl)-1,3,5-triazin-2-yl]-3-(2-trifluoromethyl-benzenesulfonyl)-urea or an agriculturally useful salt thereof to inhibit the undesirable growth of said weeds.

25. The method of claim 24, further comprising applying to the locus one or more herbicidal compounds selected from the group consisting of dicamba, diflufenzopyr, bentazon, and dimethenamid.

\* \* \* \* \*